United States Patent [19]

Rechmann

[11] Patent Number: 5,795,153
[45] Date of Patent: Aug. 18, 1998

[54] DEVICE AND METHOD FOR REMOVING DEPOSITS FROM TEETH

[76] Inventor: Peter Rechmann, Dellestrasse 79, Duesseldorf-Unterbach, Germany, 40627

[21] Appl. No.: 663,225

[22] PCT Filed: Nov. 29, 1994

[86] PCT No.: PCT/EP94/03950

§ 371 Date: Jun. 17, 1996

§ 102(e) Date: Jun. 17, 1996

[87] PCT Pub. No.: WO95/16404

PCT Pub. Date: Jun. 22, 1995

[30] Foreign Application Priority Data

Dec. 17, 1993 [DE] Germany .................. 43 43 218.2

[51] Int. Cl.[6] .................................................. A61C 15/00
[52] U.S. Cl. ............................................. 433/216; 433/215
[58] Field of Search .................................. 433/215, 216

[56] References Cited

U.S. PATENT DOCUMENTS

| | | | |
|---|---|---|---|
| 4,818,230 | 4/1989 | Myers et al. | 433/215 |
| 4,940,411 | 7/1990 | Vassiliadis et al. | 433/215 |
| 4,950,267 | 8/1990 | Ishihara et al. | 606/12 |
| 5,118,293 | 6/1992 | Levy | 433/215 |
| 5,246,436 | 9/1993 | Rowe | 606/13 |
| 5,456,603 | 10/1995 | Kowalyk et al. | 433/215 |
| 5,501,599 | 3/1996 | Rechmann | 433/216 |

FOREIGN PATENT DOCUMENTS

| | | |
|---|---|---|
| 0515983 | 12/1992 | European Pat. Off. |
| 3841503 | 6/1990 | Germany |
| 4014303 | 5/1991 | Germany |
| 4015066 | 11/1991 | Germany |

*Primary Examiner*—John J. Wilson
*Attorney, Agent, or Firm*—Diller, Ramik & Wight, PC

[57] ABSTRACT

In a device for the removal of deposits (8,10,12) on teeth (2), comprising a laser light source for a pulsed laser light beam, provided with a light conductor leading to an applicator, it is provided that the laser light source emits a laser light beam having a wavelength from 300 to 600 nm and an energy density of 0.5 to 10 $J/cm^2$.

20 Claims, 5 Drawing Sheets

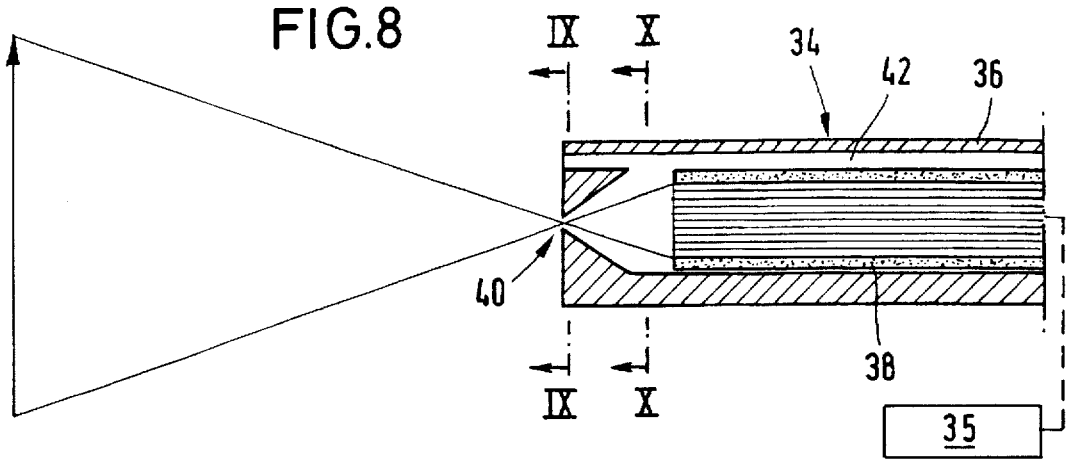
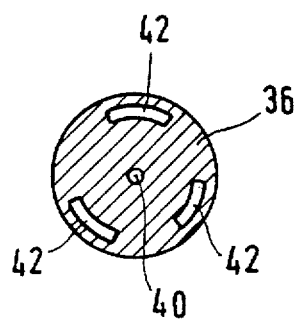 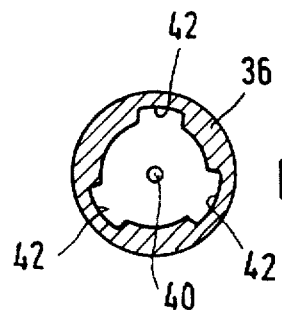
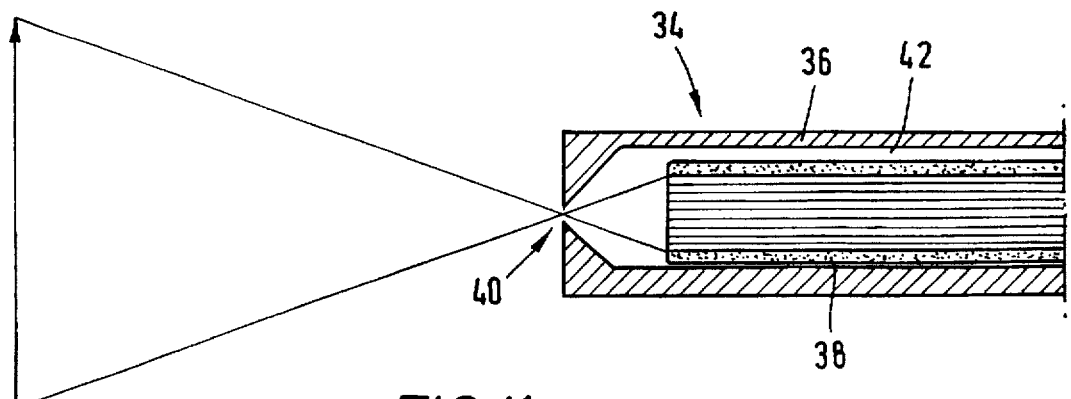

DEVICE AND METHOD FOR REMOVING DEPOSITS FROM TEETH

The present invention is directed to a device and a method for removing microbial plaque, tartar and concrements from a tooth according to the preamble of claim 1 and claim 20, respectively.

BACKGROUND OF THE INVENTION

Tartar and concrements are usually removed mechanically by use of ultrasonic instruments and hand-held instruments. When using ultrasonic instruments, the vibrating movements of the instrument tip will cause the calcified structures to split off. Nonetheless, small mineralized partial regions will remain on the surface of the tooth and enhance a rapid new deposits of plaque with subsequent crystallization into renewed tartar. Complete removal of tartar is possible by additional use of hand-held instruments. For this purpose, use is made of scalers etc. which have to be manually pulled across the surface of the tooth while exerting pressure. When performing the removal by ultrasonic devices, a disadvantage resides in that the instrument tip, due to its vibrations, may possibly damage the hard substance of the tooth. Also the use of hand-held instruments may result in damage to the hard substance of the tooth, especially if the instrument is not guided parallel to the tooth surface. Such damages are inevitable because it is not possible to perform the scraping tangentially to the tooth surface on all regions of the tooth.

In the bottom region of the gingival pocket of a tooth, complete removal of concrement is difficult already because even a hand-held instrument of the smallest possible width is still very large in comparison to the width of the gingival pocket between the tooth and the gingiva. To be able to remove all of the concrements, the instrument has to reach under the concrements and, in the process, will detach the uppermost fibers of the tooth holding structure. Thus, in case of deeper gingival pockets of a depth of e.g. more than 4 mm, especially in multirooted teeth, removal of concrements is performed under visual inspection, i.e. after folding up the gingiva by a surgical intervention.

It is already known (Aoki, A. et al: Basic Studies on the Application of Er:YAG Laser to Scaling, Proceedings of the ISLD. Third International Congress on Laser in Dentistry, Salt Lake City, Utah, 1992) to use an Er:YAG laser for the removal of concrements in the subgingival region (root smoothing). The laser light source, having a wavelength of 2.94 μm, is operated at a maximum frequency of 10 Hz and a pulse length of 200 μs. At an energy below 10 mJ/pulse, the efficiency of this laser device is very poor. Only at a higher energy between 20 and 30 mJ/pulse and at a pulse frequency of 10 Hz, an acceptable efficiency can be reached, with the resultant disadvantage that the cement layer at the root of the tooth is damaged. With energies above 30 mJ/pulse, the damages to the root of the tooth are even severe. A further disadvantage resides in the risk of possible damages to the gingiva.

Said known laser device has a high water absorption characteristic. This has the effect that, when the laser light beam is directed onto the pocket wall or the pocket bottom of the gingival pocket—which can always occur due to restricted anatomical space conditions—these tissue structures may be removed in an uncontrolled manner even when using the lowest possible laser flux densities.

From the publication "Zahnärztliche Praxis", No. 2, 1990, pages 75/76, it is known to use an excimer laser for cleaning the root canals and for removing odontalgia. The wavelength of the laser light is 308 nm. This laser device is operated at a high energy density and thus can be used like a drilling tool which removes odontalgia.

DE 39 36 714 A1 describes a water pick wherein two flexible light conductors are arranged in a hose line between the liquid pump and a handpiece, serving for the currentless transmission of switch functions to the electric motor of the liquid pump.

SUMMARY OF THE INVENTION

It is an object of the invention to provide a device for removing plaque, tartar and concrements which removes the undesired substances selectively and with a high efficiency without causing damage to the surface of the tooth or the gingiva.

The above object is solved by the features indicated in claim 1.

According to the invention, it is provided in an advantageous manner that the laser light source used for the removal of deposits and of root cement affected by bacterial infection, emits a laser light beam having a wavelength of 300 to 600 nm, preferably from 320 to 410 nm, selectively adapted to the absorption behavior of the substances to be removed and having an energy density of 0.5 to 10 J/cm$^2$ which causes no damage the gingiva and the healthy tooth substance.

The selection of the combination of the laser parameters allows for a high efficiency of the ablation of microbial plaque, tartar and concrements without causing unnecessary damage to the tissue of the gingival pocket or the healthy tooth substance, e.g. enamel under supragingival tartar, as well as enamel, healthy root cement and healthy root dentin under supragingival tartar. The inner wall of the pocket and the periodontal holding structure are not damaged when the laser light beam impinges on the pocket wall or the pocket bottom. The energy flux densities are suitably selected to preclude such damage, especially with respect to the absorption behavior of the substances to be removed at the above mentioned wavelengths of the laser light. Thus, it is possible to selectively remove the undesired deposits on teeth without damaging the gingiva or the healthy tooth substance. Further, it is possible to remove root cement affected by bacterial infection so that a regeneration of the tooth holding structures can be initiated.

The pulse length of a laser light pulse or of a Q-switched spike pulse can be less than 10 μs, and preferably is between 5 ns and 5 μs. The pulse length of the laser light should not exceed 10 μs since, otherwise, thermal damage to the adjacent tissue could not be excluded. Preferred use is made of pulse lengths in the range between 50 ns and 300 ns. It is also possible to keep to pulse length of the laser light variably adjustable in the above mentioned ranges.

Particularly preferred are pulse lengths in the range between 150 and 250 ns.

Also in free-running operation, the laser light pulses can be provided as a sequence of spike pulses having a nominal pulse length of several 100 μs.

The pulse repetition frequency of the laser light pulse of the laser light source is in the range of 10 and 200 Hz, and preferably is between 15 and 150 Hz.

Under the above provision, each pulse chain of the laser light pulse can contain 2 to 30 Q-switched spike pulses, each of them having an energy density within the claimed range.

The working point of the laser light beam can be cooled by a well-aimed liquid jet.

In this regard, a particularly preferred embodiment provides that the laser light beam is embedded in a liquid jet and is discharged from the applicator coaxially with said liquid jet. In this case, the laser light beam exactly follows the course of the liquid jet which serves as an extension of the light conductor. Thus, the working point of the laser light beam is identical with the point of impact of the liquid jet, thereby achieving that the detached deposits can be directly washed off by the liquid jet and that the sites undergoing treatment are cooled. The laser light energy density remains constant over a given portion of the liquid jet. Thus, the applicator can be used also at a distance from the working point. This is of interest for the supragingival region, whereas in the gingival pocket, because to the restricted space conditions, the applicator with the discharge nozzle for the liquid jet and the laser light beam is applied directly to the surface to be treated. This offers the advantage that no burn-off of the light conductor end can occur.

It can be provided that the applicator has its free end formed with an outlet opening for the laser light beam extending laterally of the longitudinal axis of the applicator. A lateral outlet opening for the laser light beam and respectively the liquid jet with an embedded laser light beam facilitates the removal of deposits in the narrow confines of the gingival pocket. The lateral outlet opening can be realized e.g. by a corresponding curvature of the liquid channel forming an extension of the light conductor.

The applicator can be provided with an acoustic sensor. The acoustic sensor serves for monitoring the progress of the operation since, as long as deposits still exist, the removal will generate a sound due to the ablation pressure. As soon as no deposits exist anymore, the sound level—which can be acoustically monitored by sensors—will decrease noticeably.

For controlling the success of the operation, also a control device with an optical sensor can be provided. This control device can be arranged separately in a further handpiece or on the applicator.

In a preferred embodiment, it is provided that the optical sensor is equipped with an aperture plate. Advantageously, an aperture plate can be manufactured with considerably smaller dimensions as compared to a lens. Since the laser provides for a sufficient light intensity in the operating region of the applicator, an aperture plate is fully sufficient for generating a good-quality image of the operating region.

Preferably, an image light conductor is arranged between the optical sensor and the aperture plate. Such an image light conductor consists of a plurality of bundled light conductors extending in parallel to each other. The image light conductor makes it possible to hold the optical sensor at a distance from the gingival pocket.

The aperture plate of the optical sensor can have liquid flowing therethrough. The liquid can be guided through the aperture plate itself and/or through the edge region of the aperture plate. In this regard, it is preferred that the optical head containing the aperture plate is immersed in liquid at all times. If the aperture plate itself is subjected to a liquid flow therethrough, this measure will advantageously prevent that the aperture plate becomes clogged with the deposits removed by the applicator.

In a particularly preferred embodiment, integration of an acoustic sensor into the applicator is accomplished in that the laser-light-beam-conducting liquid jet discharged from the applicator transmits the body sound generated in the working point of the laser light to an acoustic sensor in the opposite sense to the flow direction of the liquid. This body sound signal has a very low level when all of the deposits have been removed, and a correspondingly higher level when the removal of deposits is still in progress.

An embodiment of the invention will be explained in greater detail hereunder with reference to the drawings.

BRIEF DESCRIPTION OF THE DRAWINGS

FIG. 8 is a view of an optical monitoring instrument, FIGS. 9 and 10 are sectional views along the line IX—IX and resp. X—X in FIG. 8, and FIG. 11 is a view of a second embodiment of an optical monitoring instrument.

FIG. 1 illustrates a tooth 2 held in a jaw 14.

Figure 1:
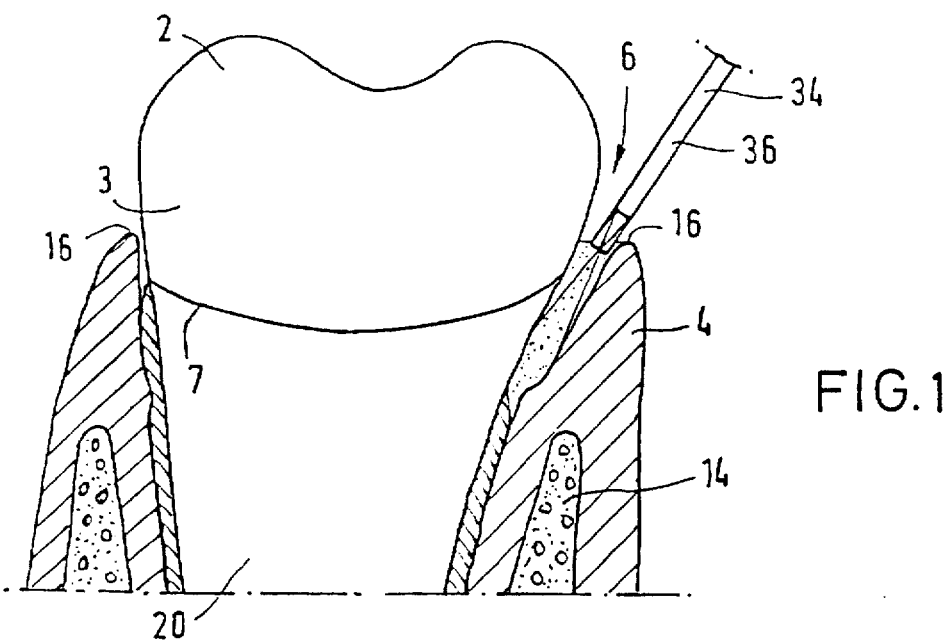
FIG. 1 is a view of a tooth with an instrument guided into the gingival pocket.

On the left side of tooth 2, healthy periodontal conditions are illustrated. In the healthy conditions, the line of adhesion of the gingiva 4 is located on the borderline 7 between the corona dentis 3 and the root cement 20. The upper edge 16 of the gingiva is situated 0.5 to 2 mm above this borderline 7, thus forming a natural gingival pocket 6 of 0.5 to 2 mm. On the right side, an affected condition is shown. Due to inflammatory processes, the bottom of the pocket is not located in the region of the borderline 7; instead, a deepened gingival pocket 6 has formed. The gingiva 4 now adheres to the tooth 2 farther below the borderline 7.

Deposits on teeth occur above and below the upper edge of the gingiva and substantially consist of tartar 8, microbial plaque 10 and concrements 12. If the gingival pocket 6 and the gingiva 4 are inflamed, also the supporting structure of the jawbone 14 will recede, so that the periodontosis in its advanced stages will result first in a loosening of the tooth and finally in loss of the tooth.

The tooth 2 comprises a corona dentis 3 covered by an enamel layer 5. On a borderline 7 located slightly above the upper edge 16 of the gingiva, the enamel layer 5 merges into the root cement layer 20.

Microbial plaque 10 consists of a bacterial aggregation of on teeth 2, which aggregation is not mineralized and contains bacteria, leukocytes, scaled-off oral epithelial cells, hemocytes and residual food particles. A plaque volume of 1 $mm^3$ contains about $10^8$ bacteria. The intermicrobial matrix (25% by volume) consists of proteins, carbohydrates and lipides. These substances originate from the bacterial metabolism, the saliva and the tissue exudate, i.e. the pocket exudate. A difference can be made between supra- and subgingival plaque. The term "supragingival" designates the region above the edge 16 of the gingiva, i.e. the visible tooth region, while the term "subgingival" designates the region within the gingival pocket 6.

The gingival pocket 6 can be defined as follows:

In upward direction, the gingival pocket 6 is either open or closed by supragingival plaque or tartar 8. The inner sides of the gingival pocket 6 consist of a pocket epithelium which is possibly affected by inflammatory proliferations. On the side of the tooth, the root dentin 18 has a layer of root cement 20 arranged thereon, which can be partially permeated by bacteria or bacterial toxins. This root cement layer 20 can be followed by a concrement layer 12 and a plaque layer 10. In downward direction, the gingival pocket is limited by the pocket wall 22, connective-tissue fibers and an epithelial layer. In the advanced stages of inflammation of the gingival pocket due to periodontosis, the pocket wall will recede farther downwards.

Tartar 8 consists of mineralized plaque, i.e. of inorganic salts including Ca/P as their principal elements. Subgingival tartar is also referred to as concrement 12, with the concrements 12 containing a larger portion of hemoglobins and thus, as to their color, having rather a dark or even black hue. The black color is partially caused by insoluble iron sulphide generated from bacterial hydrogen sulphide and salivary iron. Supragingival tartar 8, on the other hand, has a whitish yellow to dark yellow color.

Figure 2:
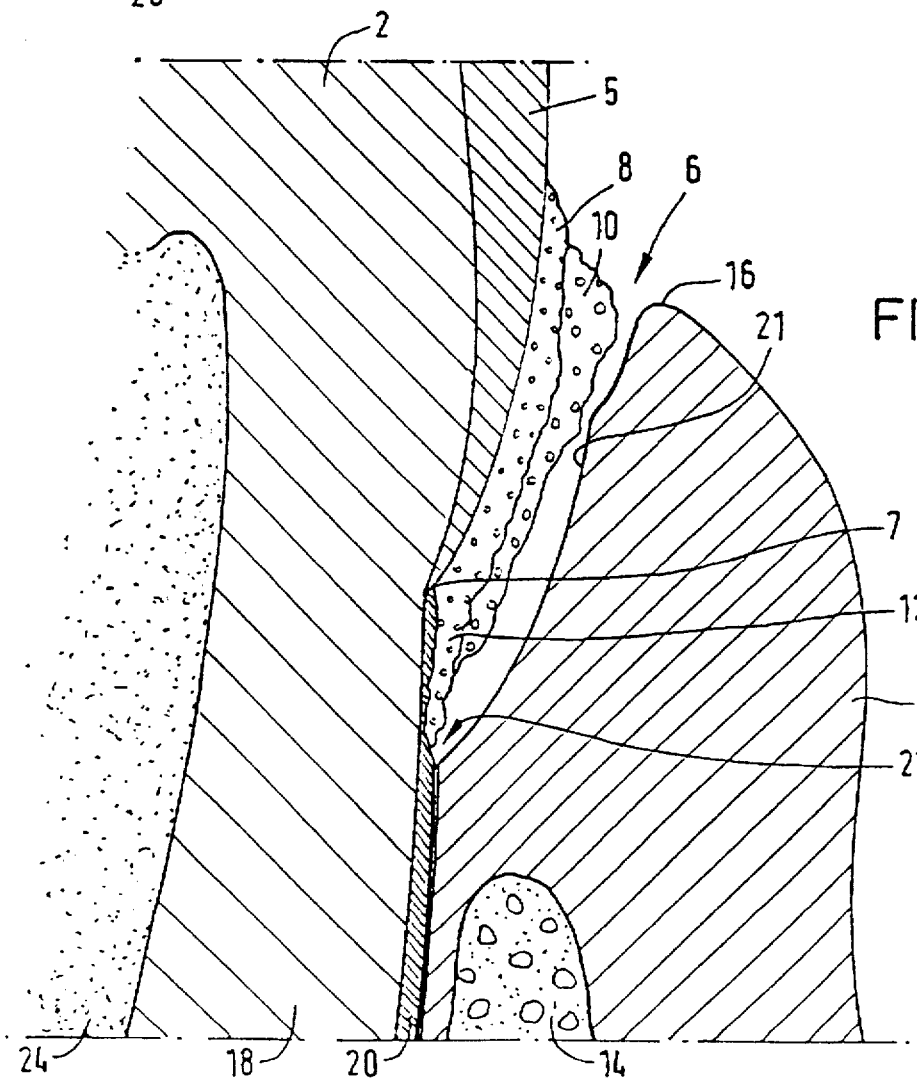
FIG. 2 is a view of the operating region of the device of the invention on the surface of the tooth.

FIG. 2 is a sectional view taken in the region of an inflamed gingival pocket 6. To the side of the root dentin 18, the cavity of tooth 2 for the pulpa 24 is shown.

Figure 5:
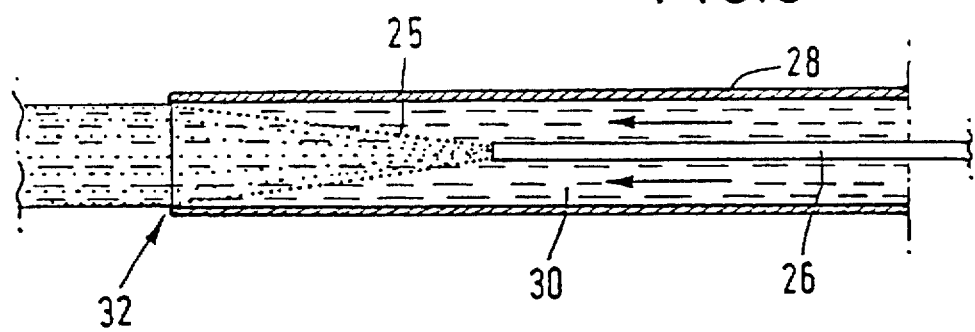
FIG. 5 is a systematic illustration of the functional principle of an applicator according to the invention.

The removal of deposits from tooth 2 is performed with a device comprising a laser light source (not shown) which—through a light conductor 26 and an applicator 28—emits a pulsed laser light beam 25 onto the tooth surface affected by deposits (FIG. 5). The applicator 28 preferably consists of a handheld instrument, the tip thereof having a diameter of about 1 to 1.5 mm to allow introduction into the gingival pocket 6.

The laser light source generates a pulsed laser light beam 25 having a wavelength from 300 to 600 nm and an energy density of 0.5 to 10 J/cm$^2$. A laser light beam with these parameters is useful for selective removal of deposits 8,10, 12 from tooth 2 without damaging the healthy hard tooth substance, e.g. enamel under supragingival tartar 8 or odontalgia, healthy root cement and healthy root dentin under subgingival tartar 8,12. Also the tissue of the gingival pocket and the adjacent tooth holding structure is left unhurt. The selective removal of the deposits is possible because of the natural absorption behavior of the deposits in the above mentioned range of wavelengths.

Figure 3:
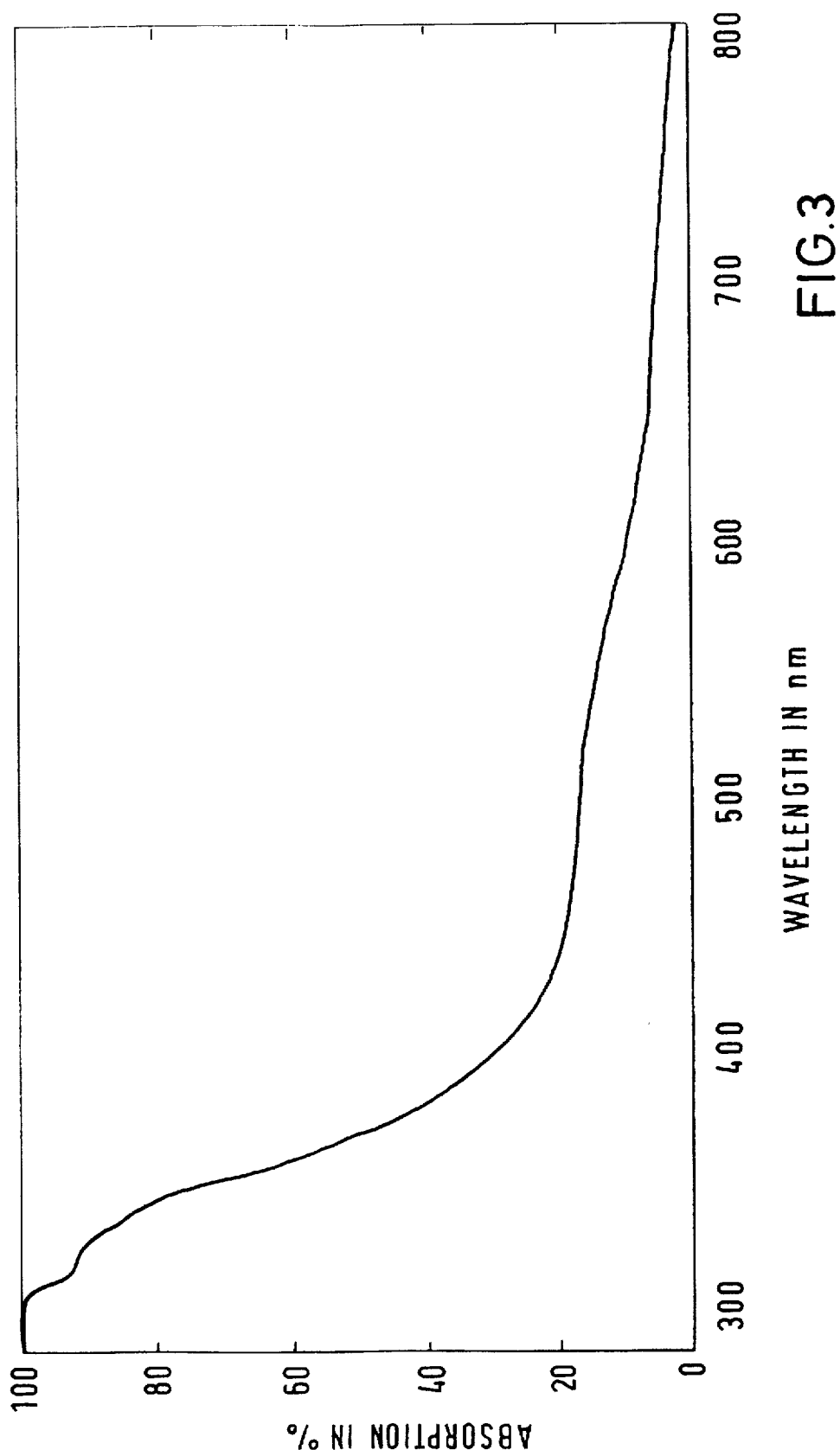
FIG. 3 is an absorption diagram for bacteria.

In the microbial plaque 10, bacteria are dominant. FIG. 3 shows an absorption diagram of a strain of bacteria known as pseudomonas areogenosa. Plotted in this Figure is the absorption intensity in dependence on the wavelength of the laser light indicated in nm. Above a wavelength of 600 nm, the absorption is only small whereas a heavy increase of absorption can be observed in wavelengths below 400 nm. This can be attributed to the characteristic absorption spectra of aromatic amino acids and of enzymes of the respiratory chain, such as NA, NEATH, cytochrome and flavoproteins etc. Typical absorption spectra of a yellow enzyme show a maximum absorption at 370 and 480 nm. With cytochrome, maximum absorption occurs at 400 nm and 550 nm.

Especially the strains of bacteria known as porphyromonas gingivalis and prevotella intermedia, also referred to as black-pigmented bacteroides, are considered to be periodontally pathogenic. The content of protoporphyrin IX (PPIX) is characteristic. Protoporphyrin absorbs light preferably at 410 nm and at 520 nm.

The content of bacteria in microbial plaque 10 is the reason for the possibly slightly larger absorption in the near range of the UW spectrum.

The absorption behavior of supragingival tartar is considerably influenced by the massive presence of bacteria and thus largely corresponds to the absorption behavior of microbial plaque 10. Microbial plaque 10, however, contains only few blood constituents which influence the absorption characteristic, but the microbial plaque 10 and thus also the supragingival tartar 8—as a form of the mineralized plaque—do contain iron and sulphur. These will form insoluble iron sulphide which has a black color and thus absorbs light within the whole spectral range.

In the concrements 12, i.e. the supragingival tartar, the high portion of inclusions of blood and blood constituents contribute to an absorption behavior wherein the maximum absorption occurs in the range between 380 and 410 nm and at 560 nm. Thus, in this case, the removal of concrements could also be performed by a laser emitting in the visible spectral region, e.g. a short-pulsed argon laser. Typically, however, presently available lasers are exclusively designed for continuous emission, which are not useful due thermal side effects.

Preferably, for a laser light source, there is used a frequency-doubled alexandrite laser with a wavelength of 380 nm or a frequency-tripled Nd:YAG Laser with a wavelength of 355 nm.

Good results can be obtained in a wavelength range between 320 and 410 while using an energy density from 1 to 5 J/cm$^2$. When using laser light of a wavelength of 380 nm, particularly advantageous use can be made of an energy density of about 3 J/cm$^2$. This combination of parameters ensures that the laser energy density with respect to said wavelength will lie below the ablation threshold of the healthy dentin 18 and thus also below the ablation threshold of the healthy enamel 5 which in turn is higher than that of dentin. This allows for selectively removal of the deposits on tooth 2. Also the root cement layer, as far as infected with bacteria, is removed. This is essential because only non-infected root cement or dentin surfaces are adapted for renewed development of cementoblasts thereon, which will regenerate the tooth support structure.

Further, the laser light can be applied selectively relative to the tissue in the gingival pocket 6. The inner wall of the pocket and the periodontal holding structure are not influenced negatively when the laser light beam impinges onto the pocket wall 21 or the pocket bottom 22. The use of a laser light beam for the removal of deposits offers the additional advantage that the laser light beam will either immediately destroy the bacteria in the gingival pocket 6 or disturb their metabolism, resulting a disinfection of the whole pocket region.

Preferably, the laser light source emits laser pulse chains of Q-switched spike pulses having a spike frequency between about 50 and 400 spikes/s. The number of spike pulses within the pulse chain lies in the range between two and thirty Q-switched spike pulses. The distance in time between the individual spike pulses is about 30 µs–50 µs. The use of successive Q-switched spike pulses advantageously allows for a better utilization of energy and makes it possible to use higher frequencies without requiring a larger transformer for the laser light source for this purpose.

If required, the pulse length of the laser light beam 25 can be variably adjusted. On doing so, the pulse length should not exceed 10 µs since, otherwise, a thermal damage to the adjacent tissue cannot be excluded. The preferred pulse length to be used is about 200 ns. With a pulse length of the laser light above 200 ns, use can be made of an increase factor for the energy density which is proportionate to the root of the quotient of the set pulse length and a base pulse length of 200 ns. Preferably, the proportionality factor is 1. This means that in case of pulse lengths above 200 ms, an energy density that has been raised corresponding to the increase factor is required in the light spot.

Instead of using pulse chains comprising a plurality of Q-switched laser light spikes, it is also possible to use pulse chains comprising uncontrolled successive laser light spikes, each pulse chain being followed by a dark phase of a duration of several ms.

The laser light pulses used for selective ablation of deposits are conducted to the applicator 28 by a light conductor 26.

From a pulse frequency of about 12 Hz onwards, the working point should be cooled in the light spot of the laser light beam. For this purpose, use can be made of a known water spray cooling device which can be mounted on the applicator 28.

Still more preferably, the laser light beam is integrated into a liquid jet 30 in the applicator 28 and to use the liquid jet as an extended light conductor when issuing from applicator 28.

FIG. 5 is a systematic representation of the integration of the laser light into the liquid jet 30. In this configuration, the free end of light conductor 26 is set back relative to the outlet opening 32 of applicator 28 to such an extent that, under consideration of the opening angle of the laser light cone, the laser light cone at the outlet opening 32 of applicator 28 will reach exactly the opening width of the outlet opening 32. The diameter of applicator 28 should be 1.0 to 1.5 at the most. Up to this diameter, applicators of various diameters can be used so that even deep gingival pockets 6 can be easily accessed. For this purpose, it would also be possible to deliver an applicator with exchangeable tip portions of different diameters.

Figure 6:
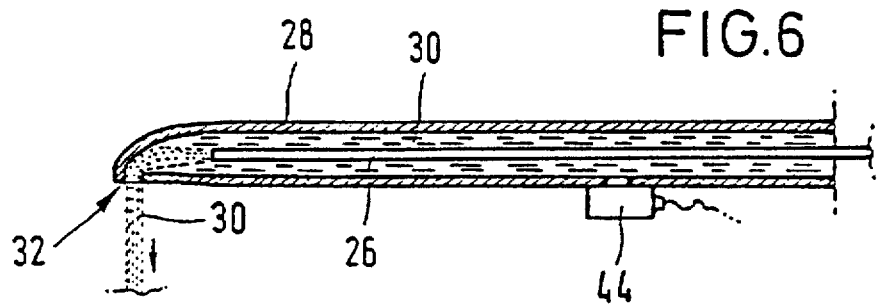
FIG. 6 is a general view of a second embodiment of an applicator with lateral jet discharge.
Figure 7:
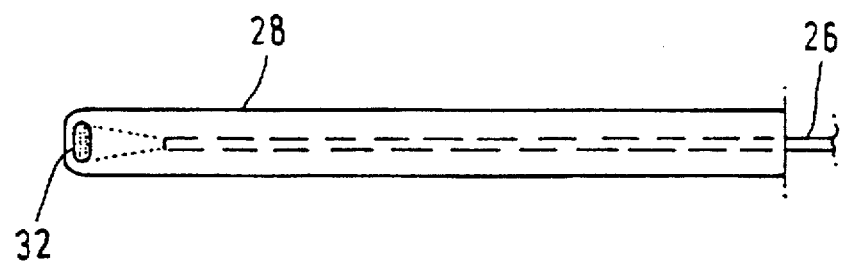
FIG. 7 is a view of the lateral outlet opening of a third embodiment of the applicator, having an oval cross section.

FIGS. 6 and 7 show a applicator with lateral discharge, which is adapted to reach also hardly accessible regions, e.g. root furcations. The above applicators 28 can be provided with ceramics-coated hollow conductors. In the embodiment of FIG. 7, there is shown an elliptic outlet opening allowing an areal treatment of the tooth surface.

Figure 4:
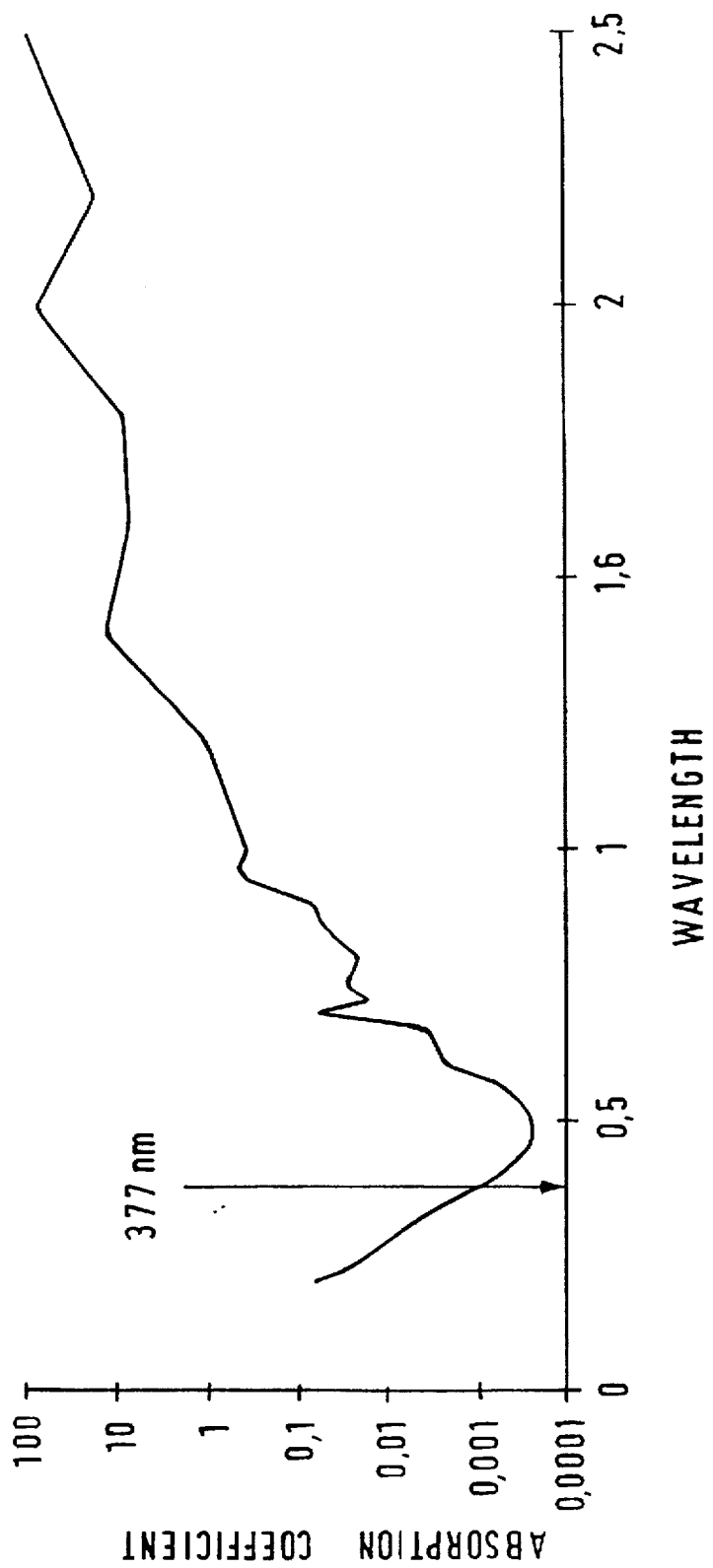
FIG. 4 is an absorption diagram for water.

The water cooling performed by the liquid jet 30 with the enclosed laser light beam 25 offers the advantage that the cooling is obtained exactly in the working point of the laser light beam. Advantageously, as evident from the absorption spectrum for water according to FIG. 4, practically no laser light absorption through water occurs in the used range of wavelengths. In this regard, the ablation is not impaired by the water contained in gingival pocket 6.

The monitoring of the ablation can be performed through fiberoptic means using an optical monitoring instrument 34. The monitoring instrument 34 is a separate hand-held instrument which can be used independently from applicator 28 and is shown in FIG. 1, by way of example, during inspection of gingival pocket 6.

FIG. 8 shows a first embodiment of an optical monitoring instrument 34, comprising an optical sensor 35, not shown, which is connected through an image light conductor 38 to the hand-held piece 36. Image light conductor 38 consists of a bundle of light conductors, other than a sole light conductor, is capable of transmitting image information. Image light conductor 38 terminates at a distance from an aperture plate 40 which is used for generating an image of gingival pocket 6 on image light conductor 38. Handheld piece 36 further includes at least one channel 42 for a rinsing liquid which is discharged from the hand-held piece 36 either—as is the case in the embodiments of FIGS. 8 to 10—in the peripheral region of aperture plate 40 and via aperture plate 40 itself, or—in the embodiment of FIG. 11—is discharged only via aperture plate 40 itself. Image transmission is enhanced by the water discharge because the gingival pocket 6 is filled with water anyway. Due to the laser light of the applicator, the tooth surface is illuminated with high light intensity so that the aperture can generate a sharp and bright image of the tooth surface.

A further possibility for monitoring the progress and the success of the operation resides in the provision of an acoustic sensor on applicator 28 for picking up the ablation sounds. In as far deposits still exist on the tooth surface, noises will be generated during ablation because of the ablation pressure, while no noises will be detectable when the tooth surface has been cleaned. In this regard, in an applicator according to the embodiments of FIGS. 5 to 7, is particularly advantageous to detect the rebounding body sound in liquid jet 30 by use of an acoustic sensor 44, which is best suited to pick up the ablation noise via the body sound.

What is claimed is:

1. A device for the removal of deposits on teeth (2) comprising a laser light source for generating a pulsed laser light beam (25), said laser light source including a light conductor (26) leading to a hand held applicator (28), means for adjusting the wavelength of said laser light source to a value in the range from 300 to 600 nm in correspondence to absorption behavior of the deposits such that said deposits are selectively removed, the laser light source having an energy density of 0.5 to 10 J/cm$^2$ in the light spot, said applicator (28) enclosing the pulsed laser light beam (25) in a liquid let (30), said applicator (28) being constructed and arranged to discharge the pulsed laser light beam (25) and the liquid let (30) coaxially, and said applicator (28) includes a discharge tip having a diameter substantially within the range of 1 to 1.5 mm to allow introduction thereof into a gingival pocket (6) of an associated tooth.

2. The device according to claim 1, characterized in that one of (a) the pulse length of a laser light pulse of the laser light beam (25) and (b) the spike pulse of a pulse chain of a laser light pulse is less than 10 µs.

3. The device according to claim 1, characterized in that the pulse length of the laser light beam (25) is between 50 and 300 ns.

4. The device according to claim 1, characterized in that the pulse repetition frequency of the laser light source is between 10 and 200 Hz.

5. The device according to claim 1, characterized in that a pulse chain of a laser light pulse contains two to 30 Q-switched spike pulses.

6. The device according to claim 5, characterized in that each laser light pulse contains two spike pulses.

7. The device according to claim 5, characterized in that the distance in time between multiple spike pulses is about 30 µs.

8. The device according to claim 1, characterized in that pulse chains comprising a plurality of laser light spikes follow each other in an uncontrolled manner, and each pulse chain is followed by a dark phase of a duration of several ms.

9. The device according to claim 1, characterized in that the laser light of the laser light beam (25) has an energy density in the light spot between 0.5 and 5 J/cm$^2$.

10. The device according to claim 1, characterized in that the laser light of the laser light beam (25) has a wavelength between 355 and 390 nm.

11. The device according to claim 1, characterized in that the energy density of the laser light beam (25) in the light spot is between 0.6 and 3.6 J/cm$^2$.

12. The device according to claim 1, characterized in that the applicator (28) has its free end formed with an outlet opening (32) for the laser light beam (25) extending laterally of the longitudinal axis of the applicator (28).

13. The device according to claim 1, characterized in that the applicator (28) has an acoustic sensor (44) arranged thereon in a manner allowing measurement of ablation noises indicating the progress of the operation.

14. The device according to claim 1, characterized in that a monitoring means (34) comprising an optical sensor (35) is one of (a) arranged on the applicator (28) and (b) as a separate hand-held piece (36).

15. The device according to claim 14, characterized in that an aperture plate (40) is arranged before said optical sensor (35).

16. The device according to claim 15, characterized in that an image light conductor (38) is connected between the optical sensor and the aperture plate (40).

17. The device according to claim 14, characterized in that a rinsing liquid passes through the aperture plate (40) of the optical sensor to enhance the image transmission through the aperture plate (40).

18. The device according to claim 1, characterized in that the liquid jet (30) transmits body sound as an acoustic signal to an acoustic sensor in the opposite sense to the flow direction of the liquid.

19. A method of removing deposits on teeth (2) through the use of a pulse laser light beam (25) by utilizing a laser light beam (25) having a wavelength adapted to the absorption behavior of tooth deposits (8, 10, 12) which are to be removed in such a manner that the energy density of the laser light beam is below the ablation threshold for healthy dentine (18), and the laser light beam (25) is utilized as a pulse chain of a plurality of laser light spikes following each other in an uncontrolled manner with each pulse chain being followed by a dark phase kept at a duration of several ms.

20. The method as defined in claim 19 wherein the laser light beam (25) has an energy density between 0.5 and 5 J/cm$^2$.

* * * * *